(12) United States Patent
Dos Santos Alves et al.

(10) Patent No.: US 7,850,849 B2
(45) Date of Patent: Dec. 14, 2010

(54) ANAEROBIC REACTOR FOR THE REMOVAL OF LONG CHAIN FATTY ACIDS FROM FAT CONTAINING WASTEWATER

(75) Inventors: Maria Madalena Dos Santos Alves, Braga (PT); Merijn Amilcare Picavet, Porto (PT); Maria Alcina Alpoim De Sousa Pereira, Guimarães (PT); Diana Zita Machado De Sousa, Oliveira de S. Mateus (PT); Ana Júlia Viana Cavaleiro, Braga (PT)

(73) Assignee: Universidade Do Minho, Braga (PT)

( * ) Notice: Subject to any disclaimer, the term of this patent is extended or adjusted under 35 U.S.C. 154(b) by 236 days.

(21) Appl. No.: 12/094,223

(22) PCT Filed: Nov. 18, 2005

(86) PCT No.: PCT/PT2005/000020
§ 371 (c)(1),
(2), (4) Date: Aug. 29, 2008

(87) PCT Pub. No.: WO2007/058557
PCT Pub. Date: May 24, 2007

(65) Prior Publication Data
US 2009/0050560 A1  Feb. 26, 2009

(51) Int. Cl.
*C02F 11/04* (2006.01)
*C02F 3/28* (2006.01)

(52) U.S. Cl. .................. 210/603; 210/194; 210/197

(58) Field of Classification Search ................ 210/603, 210/194, 196, 197
See application file for complete search history.

(56) References Cited

U.S. PATENT DOCUMENTS

| | | | |
|---|---|---|---|
| 5,616,240 A * | 4/1997 | Sonnenrein | 210/104 |
| 5,942,116 A * | 8/1999 | Clark et al. | 210/603 |
| 7,300,584 B2 * | 11/2007 | Langhans et al. | 210/629 |
| 7,708,885 B2 * | 5/2010 | Lanting et al. | 210/603 |
| 2004/0025715 A1 * | 2/2004 | Bonde et al. | 99/485 |

FOREIGN PATENT DOCUMENTS

JP   07-096298 A  *  4/1995

* cited by examiner

*Primary Examiner*—Fred Prince
(74) *Attorney, Agent, or Firm*—Sughrue Mion, PLLC

(57) ABSTRACT

The invention presented is an apparatus specifically designed for the high rate anaerobic treatment of (waste)waters with relatively high concentrations of lipidic compounds, referred to as the Inverted Anaerobic Sludge Blanket (IASB) reactor. Contrary to conventional anaerobic reactors, it avoids the need of sludge with good settling properties and exploits the problem of sludge flotation due to long chain fatty acid (LCFA) or biogas adsorption onto the sludge and/or biogas encapsulation by the sludge. Furthermore, it provides an increased specific sludge surface area for better LCFA degradation. It is fed from the top and is equipped with a separation step at the bottom. Reactor contents are thoroughly mixed by the novel combined action of a gas lift loop and a liquid recycle over the reactor. The reactor can be operated in continuous and sequential mode. Although it is specifically designed for lipid degradation, its application is not limited to this.

23 Claims, 3 Drawing Sheets

ANAEROBIC REACTOR FOR THE REMOVAL OF LONG CHAIN FATTY ACIDS FROM FAT CONTAINING WASTEWATER

FIELD OF THE INVENTION

The invention presented is an apparatus specifically designed for the high rate anaerobic treatment of (waste) waters with relatively high concentrations of lipidic compounds, referred to as the Inverted Anaerobic Sludge Blanket (IASB) reactor and a method to treat this kind of waters.

STATE OF THE ART

More and more people are becoming aware of the need for a sustainable society. Using renewable products and controlling pollution are ways to achieve sustainability. Both are combined when wastewater is biologically treated in the absence of oxygen: through the action of anaerobic bacteria organic pollutants present in wastewater are effectively converted into biogas, a gas that mainly consist of methane ($CH_4$) and carbon dioxide ($CO_2$) and is a renewable energy source. This gas can then be used to produce e.g. useful electric energy. Worldwide anaerobic technology is being successfully applied to treat effluents from e.g. breweries and the paper industry using compact wastewater treatment installations. An example of a widely spread applied anaerobic technology is the upflow anaerobic sludge blanket (UASB).

A major group of organic pollutants which has shown very difficult to be converted into biogas are the lipids. Because of this, they are usually removed from wastewater using technologies that require energy instead of producing energy. In this way, these technologies do not contribute to a sustainable society. The current invention, referred to as the Inverted Anaerobic Sludge Blanket, makes it possible to efficiently remove lipids from wastewater and convert them into useful bioenergy in the form of biogas.

The application of the invention opens up new markets for the application of anaerobic technology. Previously, industries at which wastewaters are produced with relatively high lipid content were practically off-limits. These industries include edible oil and fat refineries, olive oil mills, dairy industries, wool scouring, meat, poultry and fish processing industry.

High rate anaerobic treatment of wastewater is possible by separating the solids retention time (SRT) from the hydraulic retention time (HRT). To achieve this, different separation methods are available. It is on this principle that virtually all patented technologies concerning anaerobic treatment of wastewater are based. The difference between the technologies is the separation method applied to keep biomass inside the reactor. Between these technologies, the anaerobic membrane bioreactor (AMBR) may be considered as different, since separation is essentially based on size and not on sedimentation. Although the AMBR has been shown to be useful for e.g. continuous anaerobic sulphate reduction using extremophiles and may be used for removal of dissolved organic pollutants, they are less suitable for lipids containing wastewater due to increased membrane clogging. With the current state-of-the-art membrane technology intensive and therefore expensive cleaning regimes would be required.

Tilted plate separators (TPS) may be applied to continuously separate biomass and solids or oil from wastewater (NL patent 7208503, U.S. Pat. Nos. 4,202,778 & 4,477,344). They have been applied on a full-scale level for separating e.g. biologically produced elemental sulphur from wastewater. It is less common for them to be integrated in continuous anaerobic reactors (U.S. Pat. No. 5,904,850), especially when relatively big amounts of gas are produced or circulated. This is due to the disturbing effect of gas on the settling of solids in between the parallel tilted plates. Thus, enough degassing surface would need to be provided next to the integrated TPS to prevent disturbance of the solids settling process. This can be done by increasing the reactor surface at the top. This, however, considerably increases the costs of reactor construction compared to a simple cylindrical reactor. Another way would be simply using bigger reactors. Considering the fact that integrating the TPS in the reactor is, amongst others, contemplated as to reduce space requirements, this option may seem a bit forceful and therefore a disinvestment.

When lipids containing wastewater is anaerobically treated using high rate reactors not only considerable amounts of biogas would be produced: Due to long-chain fatty acid (LCFA) adsorption sludge flotation occurs. Top-mounted TPS are not suited to retain floating sludge within a reactor.

Three-phase separation is the most common way to maintain high solids concentrations within continuous high-rate biogas producing reactors. The most used three-phase separators are of the gas cap variety (e.g. European patents 0808805 & 1291326, U.S. Pat. No. 5,855,785). The gas caps are essentially inverted funnels in which biogas is accumulated. Wastewater continues upwards, while sludge settles back into the sludge blanket maintained in the bottom part of the reactor. The sludge blankets usually consist of granular sludge, although flocculate biomass may be applied as well. The best known high rate reactor using this technology is the upflow anaerobic sludge blanket (UASB) reactor. These reactors have up to three layers of three-phase separators in the top. Mixing is achieved through biogas production and application of an upflow velocity of typically 1 m/h.

Reactors capable of dealing with higher organic loading rates are becoming more and more common, however, and substituting the UASB reactor. Most of them still apply the same three-phase separators, however. The difference is that they are more compartmentalised. This way a lower highly turbulent zone and an upper clarification and settling zone can be created. These compartments are separated from each other by layers of three-phase separators (European patents 1408009 & 0808805, U.S. Pat. No. 4,609,460). Through this compartmentalisation more intensive mixing can be obtained by applying higher upflow velocities and recycling biogas using gas lift loops (U.S. Pat. Nos. 5,338,447 & 4,609,460, EP 1408009). Yet another way of maintaining biomass in a high-rate anaerobic reactor and intensifying the process is through immobilisation onto a carrier material, e.g. pumice. Thus, a fluidised bed is obtained. Again, intensive mixing may be achieved using a gas lift loop (U.S. Pat. No. 4,482,458) or a liquid recycle.

Separation using three-phase separators is based on sedimentation of solids: Due to their higher density solids have the tendency to settle to the lower parts of the reactor. Floatation of sludge may sporadically occur due to encapsulation or adsorption of biogas. Most of the newer high-rate reactors are equipped to deal with limited amounts of floating sludge. Usually gas lift loops are involved. These are used to suck floating sludge from above the three-phase separators back into the reactor (U.S. Pat. Nos. 4,609,460 & 5,338,447) or to swing particles from under the three-phase separator back into the reactor (U.S. Pat. No. 5,855,785). Another way is to simply provide for a separate section where particles entrained with the gas loop have a chance to settle back into the reactor compartment (EP 1408 009, U.S. Pat. No. 4,482,458). Excessive amounts of floating sludge such as occur during LCFA degradation form a severe problem for high-rate anaerobic reactors equipped with three-phase separators. They are not able to maintain sludge inside the reactor and consequently bioactivity is lost leading to eventual process failure.

Continuous processes have been patented in which not a specific separator is applied. Enough space is provided to allow for solid-liquid-gas separation. U.S. Pat. No. 6,048,459 and 2003085171 disclose processes where external gas is provided to create gas lifts for increased mixing at low shear stress. The gas lifts drag solids along and lead to quiescent zones where they may settle. Subsequently, the solids are sucked back into the reactor through the gas loop downer. Gas is collected in the head space of the reactor. It may be appreciated that due to the absence of separation equipment it is difficult to retain floating sludge within such reactors.

Another way to prevent specific separation equipment is through immobilisation of biomass onto fixed surfaces. Enough surface area has to be provided, however, as to prevent mass transport limitation. One such way is described in Spanish patent 2212895. Here tubes are used onto which biomass is fixed. Mixing is obtained using gas lift loops. Although biomass floatation and subsequent washout is obviously prevented if LCFA containing wastewater is treated, other problems are encountered when fixing biomass onto surfaces: the limited surface area onto which LCFA may adsorb. This unavoidably leads to mass transport limitation. Furthermore, the ability of biomass to attach to surfaces is severely affected by the presence of LCFA resulting in eventual detachment and washout.

As previously mentioned, biomass can also be immobilised onto particles (biocarriers) thus forming a fluidised bed. Here, two options are available: The biocarrier applied can either have a higher density (U.S. Pat. No. 4,482,458) or a lower density than water (U.S. Pat. No. 4,454,038 & 2002/0185437). When particles with a higher density than water are applied a fluidised bed in the bottom section of the reactor is formed. Floatation due to LCFA adsorption would definitely lead to sludge washout and activity loss. When particles with a lower density than water are applied an inverted floating fluidised bed is obtained. These fluidised beds are fed from the top and provided with a means for fluidisation. This can be a liquid recycle from the reactor bottom to the reactor top (U.S. Pat. No. 4,454,038). Fluidisation can also be obtained by applying a gas lift loop (U.S. patent 2002/0185437 and U.S. Pat. No. 4,454,038). In this case gas either containing oxygen or hydrogen is provided using a compressor. Furthermore, gas may be recycled using a further compressor or pump. Fluidised beds make use of bio-attachment to particles. As previously stated, the ability of biomass to attach to surfaces is severely affected by the presence of LCFA. Thus, the floating particle bed would only take up space instead of serving a definite purpose, thus reducing reactor efficiency. Preferably, biocarriers are avoided. A big part of the energy that would be generated in the form of biogas is lost to energy intensive gas compression for gas provision purposes. Gas compression is best avoided.

Instead of a continuous process a fed-batch process may be applied for LCFA removal from wastewater. The anaerobic sequencing batch reactor (ASBR, U.S. Pat. No. 5,185,079) is such a process. It may be fed with LCFA containing wastewater after which LCFA adsorbs onto the biomass present. After feeding LCFA is allowed to be broken down and the biomass is allowed to settle. The then treated water is drawn off. The ASBR prevents the problems related to LCFA adsorption encountered with continuous processes. Nevertheless, the principles of solids separation are still based on sedimentation. If mixing is applied using a fluid recycle, the recycle is applied from below as to fluidise the sludge blanket. Furthermore, the ASBR as described in U.S. Pat. No. 5,185,079 is limited to sequential operation. If operated in continuous mode the same problems with floating sludge would be encountered.

SUMMARY OF THE INVENTION

The current invention is a reaction vessel providing the means for high-rate anaerobic LCFA degradation. The reaction vessel is designed in such a way that sludge buoyancy due to LCFA adsorption and/or biogas encapsulation or adsorption are advantageously used to maintain sludge inside the reaction vessel. Contrary to conventional anaerobic techniques, neither sludge granulation nor biocarriers are used to maintain biological activity inside the reactor. In fact, it is an objective of the current invention to demote sludge granulation to increase the adsorption surface for LCFA and sludge buoyancy due to biogas encapsulation. A further objective is the inducement of a natural gas lift effect due to biogas production without the application of a compressor or pump. Yet another objective is increasing LCFA degradation efficiency by applying a liquid and sludge recycle over the reactor from bottom to top. This recycle is joined, and thus intensely contacted, with LCFA and/or other organic constituents containing influent and injected into one or more draft tubes in a downward motion, thus creating a downflow inside the draft tube(s). Due to this downflow suction is created leading to entrainment of floating sludge leading to further intense contact between sludge and reactor influent and further liberating encapsulated biogas. A still further objective is to provide an effluent virtually free of suspended solids by applying a separation step at the bottom of the reactor.

DETAILED DESCRIPTION OF THE INVENTION

Method

Figure 1:
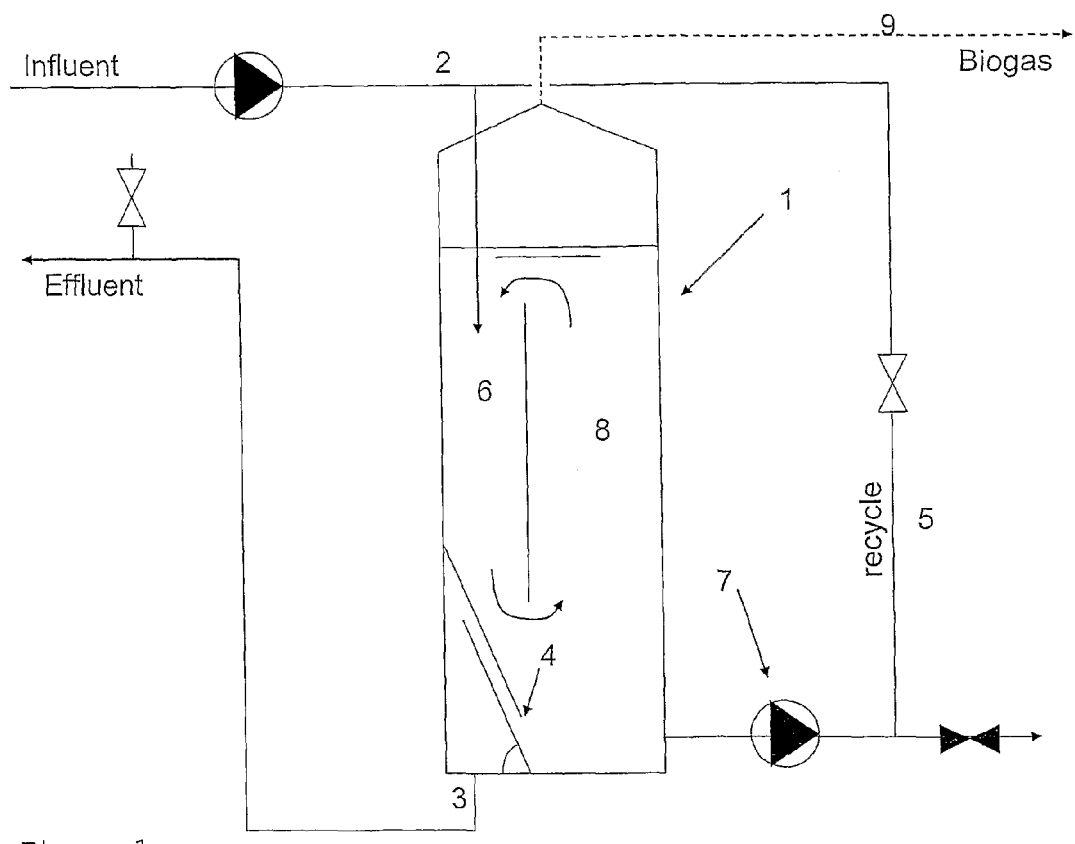
FIG. 1 shows a schematic representation of a possible configuration of the current invention.

A preferred embodiment of a process according to the present invention provides a process for the biological anaerobic treatment of wastewater by converting constituents into gaseous compounds, said process comprising:

a) Intense mixing of influent with reactor liquor extracted from the bottom section of the reaction vessel without damaging bacteria present;

b) Intense contacting of wastewater with the reactor sludge;

c) Demoting of sludge granulation to increase the contact area between bacteria and constituents to be converted into gaseous compounds without damaging the bacteria;

d) Dispersing floating sludge into the reactor without damaging the biocatalysts by injecting liquid into at least one downer;

e) Liberating encapsulated gaseous compounds by applying low shear stress;

f) Mixing of reactor contents through a natural gas lift effect induced by the production of gaseous compounds;

g) Removing gaseous compounds at the top of the reactor;

h) Separating solids from purified water using a separation step thus retaining sludge inside the reactor vessel and maintaining activity;

i) Removing purified water from the reaction vessel after said separation step;

j) Removing sludge as required from the vessel;

k) Preventing excessive foaming by spraying treated water onto the floating sludge layer;

l) Provision of influent either in a continuous mode or in a fed batch mode.

In an embodiment of the present invention the constituents to be removed from the water are lipidic compounds (long chain fatty acids (LCFA)), which induce sludge floatation after being adsorbed onto the sludge. In another embodiment of the present invention the constituents to be removed are organic compounds such as volatile fatty acids, ethanol and aromatic compounds. The gaseous compounds produced are mainly methane gas ($CH_4$) and carbon dioxide ($CO_2$) to form biogas.

In a further embodiment of the current invention adsorption is promoted by joining a sludge recycle extracted at one or more outlets at the bottom of the reactor with reactor influent, after which the mixture is downwardly injected into at least one downer. The downward injection of this flow creates suction at the top of the downer thus entraining floating sludge from the top of the reactor into the downer. This way further constituent adsorption is obtained. The flow in the downer is highly turbulent and will initially stimulate the liberation of biogas possibly encapsulated by the sludge. Nevertheless, the sludge will be dragged downward by the liquid flow.

In a yet further embodiment of the current invention after constituent adsorption, biogas is mainly produced in the compartment outside the downer: the riser section. This leads to a natural gas lift effect thus stimulating liquid circulation in the reactor. Due to biogas production and organic constituent adsorption, foaming will be induced. In an embodiment of the current invention this is counteracted by spraying treated effluent in the top of the reactor.

In a still further embodiment of the current invention the liquid level inside the reaction vessel is maintained using a vertically extended tube equipped with a siphon breaker to the required liquid level and connected to the purified water outlet(s) of the reaction vessel.

In a still further embodiment of the current invention the microbial population inside the reactor consists of anaerobic hydrolysing bacteria, acidifying bacteria, acetogenic bacteria and methanogenic bacteria. In a further embodiment the microbial population also comprises bacteria specialised in hydrolysing lipids and anaerobically oxidising long chain fatty acids.

Apparatus

A preferred embodiment of an apparatus according to the present invention is a vertically elongated reaction vessel for the biological anaerobic treatment of wastewater comprising a wastewater inlet system for reactor liquor and influent mixing and subsequent downward injection through one or more inlets or nozzles into one or more draft tubes located under the water level and mounted of the bottom of the reaction vessel, a reactor liquor recycling system comprising one or more outlets or nozzles for the suction of reactor liquor located in the bottom section of the reactor vessel, a means for recycling reactor liquor from the bottom section to the wastewater inlet system, a means for separating solids from purified water situated in the bottom section of the reaction vessel, a treated wastewater outlet system comprising one or more outlets or nozzles located after the said means for separating solids for the removal of treated water out of the reaction vessel, one or more spraying nozzles situated in the top of the reactor for spraying treated water onto the floating sludge as to counteract foaming, and a biogas collection system located in the top of the reactor above the spraying nozzles comprising one or more outlets. The apparatus is hereafter referred to as the Inverted Anaerobic Sludge Blanket (IASB) reactor.

In an embodiment of the present invention the IASB reactor has a cylindrical shape with a height to diameter ratio of at least 2, equipped with one or more cylindrical draft tubes open at both ends that serve as downers, comprising a separator consisting of two or more concentric funnel shaped surfaces with the inclined surfaces each making an equal angle with the horizontal and of which the top one is lined with the reactor wall and the bottom one is connected to the reactor bottom. The draft tubes are essentially submerged and fixed above the funnel shaped separator at such a distance to provide for a quiescent zone for non-buoyant solids to settle to the bottom from where they may be recycled to the top of the reactor or, if necessary, discharged. The draft tubes should be sized in such a way that sludge entrainment from the top and intensive mixing due high liquid flow rate are assured and appreciable biogas production in the draft tubes is prevented. Thus, the liquid residence time in the draft tubes should be limited. The total cross sectional area of the downer section is essentially smaller than the cross sectional area of the riser section. It is further possible to apply different cross sectional areas at different heights of the draft tube(s) as to stimulate sludge entrainment and create a more turbulent zone in the top (smaller cross section) and a less turbulent zone in the bottom (bigger cross section) of the draft tubes. Yet another possibility is the application of a restriction in the top section of the draft tubes. The inclined surfaces of the funnel shaped separator should have such an inclination that close to laminar flow is assured for optimum solids settling. The angle between the inclined surface and the horizontal preferably is between 50 and 75°. The treated wastewater outlet system is situated in the compartment between the cylindrical bottom section of the reactor and the outside of the lowest funnel shaped surface of the separator. The effluent system should comprise enough outlets as to prevent short circuiting over the separator and thus biomass entrainment due to preferential flows.

In another embodiment the reactor has a cylindrical shape and is equipped with a submerged wall to create two compartments, i.e. the downer and riser compartment. It is further possible to apply two walls to create different cross sectional areas at different reactor heights as to improve sludge entrainment and constituent adsorption. The reactor is further equipped with two or more inclined parallel plates serving as separator. The inclined plates are joined with the walls. Some space is allowed for between the separator and the submerged wall as to prevent turbulent conditions near the separator influent area. The angle between the horizontal and the inclined plates preferably is between 50 and 75°. The treated wastewater outlet system is situated in the compartment between the cylindrical bottom section of the reactor and the inclined plate separator. The effluent system should comprise enough outlets as to prevent short circuiting over the separator and thus biomass entrainment due to preferential flows.

In yet another embodiment of the present invention the reactor has a rectangular or other symmetrical shape other than cylindrical with the vertical length being bigger than the horizontal one, comprising one or more separator units consisting of two or more inclined parallel plates. The one or more downers may be created by applying submerged cylindrical tubes located above the separator units or by dividing the reactor into sections using submerged walls located above the separator units. The vertical spacing between riser/downer section and separation section should be such that turbulent conditions near the separator influent are prevented. It is crucial that the compartment(s) with downward flow have a smaller cross sectional area than the riser compartment(s).

The invention is in no way limited to the above described embodiments. In fact many variations on the above described embodiments are possible within the scope of the claims.

DETAILED DESCRIPTION OF THE FIGURES

A possible configuration of the present invention is shown in FIG. 1. It concerns a reactor 1 suited for sequential and continuous treatment of e.g. LCFA containing wastewater. In contrast with conventional anaerobic technology, the sludge blanket is essentially a floating blanket. It is therefore beneficial to feed the reactor from the top (2) and draw off effluent at the bottom (3). It cannot be completely prevented that some sludge settles at the bottom of the reactor. To prevent sludge washout, a separation step 4 is located at the bottom of the reactor before effluent exit points. One lamella separator consisting of two parallel plates is located at the bottom to keep the sludge inside the reactor. It is placed in such a way that gas cannot enter them and disturb the separation process. The inclined parallel plates are placed at an angle of 70° with the reactor bottom. Mixing is achieved in two ways. Firstly, reactor influent 2 is mixed with a reactor liquor recycle 5 and then injected downwards into one or more reactor downers 6. In FIG. 1 one downer is shown created using a submerged wall. The liquid recycle is drawn from the bottom of the reactor using a pump 7. It also serves to pump settled sludge from the bottom to the top. Furthermore, sludge settled at the bottom will be exposed to shear forces, thus increasing the sludge surface area. Pump 7 can also be used for periodic sludge discharges to prevent excessive solids build-up. Further mixing is provided by an internal gas lift loop due to biogas production in riser 8. Thus, liquid with sludge laden with LCFA circulates to the top of the reactor and closes the gas lift loop. This is indicates with curved arrows in FIG. 1. The downer area is essentially smaller than the riser area. This is to increase turbulence in the downer and biogas release in the riser. Biogas 9 leaves the reactor at the top. To counteract foaming due to biogas production and the presence of LCFA, the reactor may be equipped with water sprays in the top of the reactor. The water used for the sprays is the treated reactor effluent.

Figure 2A:
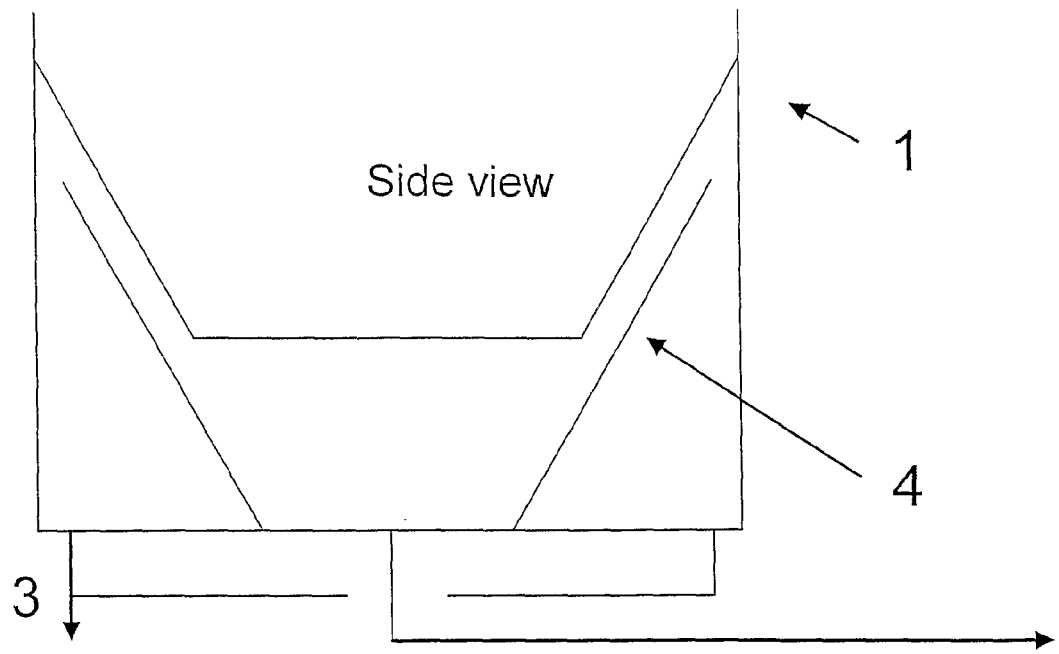
FIG. 2 shows a possible configuration of the inclined plate settler at the bottom.
Figure 2B:
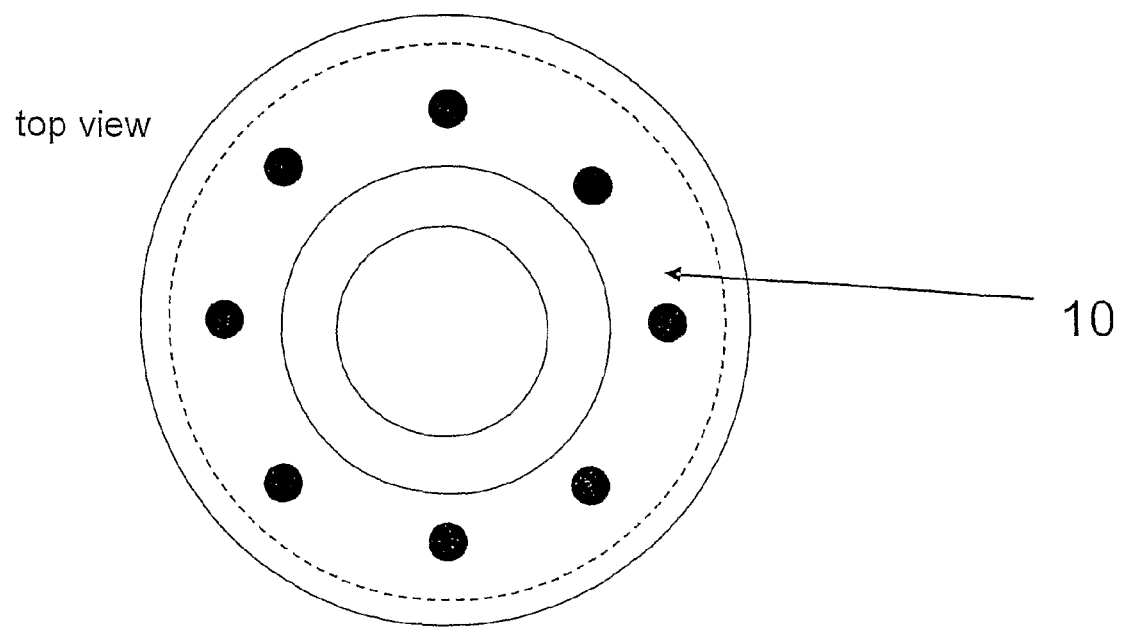

FIG. 2 shows a schematical representation of an inclined plate settler 4 consisting of two concentric funnels. It shows the side view (FIG. 2a) and the top view (FIG. 2b) of the bottom section of a reaction vessel 1. In the top view a possible configuration of outlets 10 is also schematically shown.

Figure 3A:
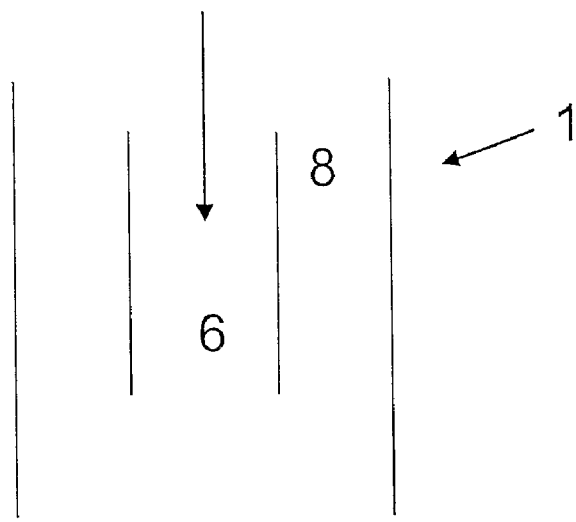
FIG. 3 shows possible draft tube configurations.
Figure 3B:
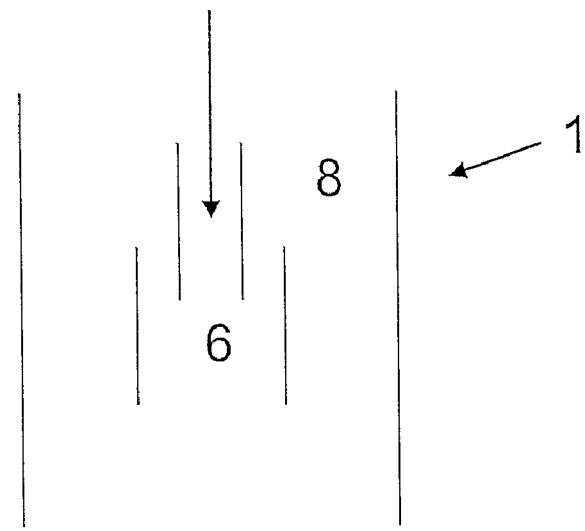
Figure 3C:
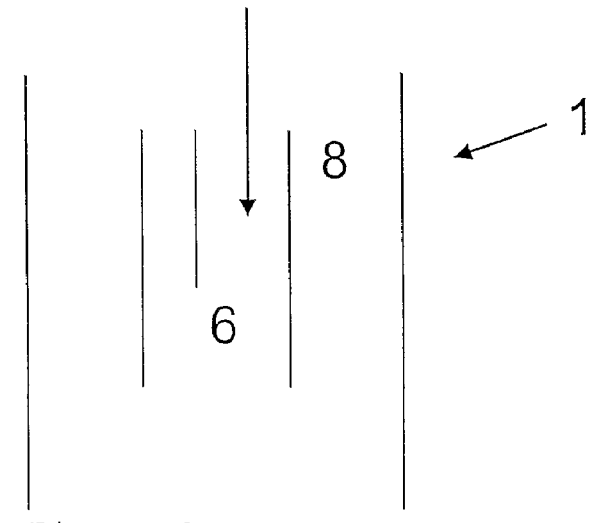

FIG. 3 shows three different draft tube configurations. FIG. 3a shows one draft tube concentric with reactor vessel 1. The arrow demonstrates the liquid flow through downer 6. The space between the downer 6 and vessel wall is the riser area 8. FIG. 3b shows a draft tube with a restriction as to increase sludge entrainment and local turbulence and adsorption. FIG. 3c shows two concentric draft tubes. Advantages of the configurations shown in FIGS. 3b and 3c are increased entrainment and initial turbulence and the possibility for liberated encapsulated biogas to freely rise to the top of the reactor without disturbing the downward liquid flow.

The invention claimed is:

1. An apparatus for biological anaerobic treatment of wastewater, comprising a vertically elongated reaction vessel (1), a wastewater inlet system for reactor liquor (5) and influent (2) mixing and subsequent downward injection through one or more inlets or nozzles into one or more draft tubes located under the water level and mounted off the bottom of said reaction vessel (1), a reactor liquor recycling system comprising one or more outlets or nozzles for the suction of said reactor liquor (5) located in the bottom section of said reactor vessel (1), a means (7) for recycling said reactor liquor (5) from the bottom section to said wastewater inlet system, a means (4) for separating solids from purified water (3) situated in said bottom section of said reaction vessel, a treated wastewater outlet system comprising one or more outlets or nozzles (10) located after the said means (4) for separating solids for the removal of treated water (3) out of said reaction vessel (1), one or more spraying nozzles situated in the top of the reactor for spraying said treated water (3) onto the floating sludge as to counteract foaming, and a biogas collection system located in the top of the reactor (1) above the spraying nozzles comprising one or more outlets.

2. The apparatus of claim 1, wherein said reaction vessel (1) has a cylindrical shape with a height to diameter ratio of at least 2, equipped with one or more cylindrical draft tubes open at both ends that serve as downers (6), comprising a separator (4) consisting of two or more concentric funnel shaped surfaces with the inclined surfaces each making an equal angle with the horizontal and of which the top one is lined with the reactor wall and the bottom one is connected to the reactor bottom.

3. The apparatus of claim 2, wherein said draft tubes are essentially submerged and fixed above the funnel shaped separator (4) at such a distance to provide for a quiescent zone for non-buoyant solids to settle to the bottom from where they may be recycled to the top of the reactor (1) or, if necessary, discharged.

4. The apparatus of claim 2, wherein said draft tubes should be sized in such a way that sludge entrainment from the top and intensive mixing due high liquid flow rate are assured and appreciable biogas production in the draft tubes is prevented.

5. The apparatus of claim 2, wherein the total cross sectional area of the downer section (6) is essentially smaller than the cross sectional area of the riser section (8).

6. The apparatus of claim 2, wherein the one or more draft tubes have different cross sectional areas at different heights to stimulate sludge entrainment and create a more turbulent zone in the top and a less turbulent zone in the bottom of the draft tubes.

7. The apparatus of claim 2, wherein a restriction is applied in the top section of the said one or more draft tubes.

8. The apparatus of claim 2, wherein the angle between the said funnel shaped surfaces and the horizontal is between 50 and 75° C.

9. The apparatus of claim 1, wherein said reaction vessel (1) has a cylindrical shape, with a height to diameter ratio of at least 2, is equipped with a submerged wall to create a downer (6) and a riser (8) compartment of which the downer area is essentially smaller than the riser area (8) and is further equipped with a separator (4) consisting of two or more inclined parallel plates which are joined with the walls and make an angle between 50 and 75° C. with the horizontal.

10. The apparatus of claim 9, wherein said wall is essentially fixed above said separator at such a distance to provide for a quiescent zone for non-buoyant solids to settle to the bottom from where they may be recycled to the top of the reactor or, if necessary, discharged.

11. The apparatus of claim 9, wherein a second wall is applied to create different cross sectional areas at different reactor heights as to improve sludge entrainment and constituent adsorption.

12. The apparatus of claim 1, wherein said reaction vessel (1) has a rectangular or other symmetrical shape other than cylindrical with the vertical length being bigger than the horizontal length, comprising one or more separator units (4) consisting of two or more inclined parallel plates.

13. The apparatus of claim 12, wherein said reaction vessel (1) has one or more downers (6) created by applying submerged cylindrical tubes located above the separator units or by dividing the reactor (1) into sections using submerged walls located above the separator units and providing for enough spacing between said cylindrical tubes or said wall to provide for a quiescent zone for non-buoyant solids to settle to the bottom from where they may be recycled to the top of the reactor (1) or, if necessary, discharged.

14. The apparatus of claim 13, wherein said one or more downers (6) essentially have a smaller cross sectional area than the one or more risers (8).

15. A method for the biological anaerobic treatment of wastewater by converting constituents into gaseous compounds, said process comprising: a) Intense mixing of influent (2) with reactor liquor (5) extracted from the bottom section of the said reaction vessel (1) without damaging bacteria present; b) Intense contacting of wastewater with reactor sludge; c) Demoting of sludge granulation to increase the contact area between bacteria and constituents to be converted into gaseous compounds without damaging the bacteria; d) Dispersing floating sludge into the reactor (1) without damaging the bio-catalysts by injecting said mixture of reactor liquid and influent into at least one downer (6); e) Liberating encapsulated gaseous compounds by applying low shear stress; f) Mixing of reactor contents through a natural gas lift effect induced by the production of gaseous compounds; g) Removing gaseous compounds (9) at the top of the reactor (1); h) Separating solids from purified water using a separation step (4) thus retaining sludge inside the reaction vessel (1) and maintaining activity; i) Removing purified water (3) from the reaction vessel (1) after said separation step (4); j) Removing sludge as required from the vessel (1); k) Preventing excessive foaming by spraying treated water (3) onto the floating sludge layer; l) Provision of influent (3) either in a continuous mode or in a fed batch mode.

16. The method of claim 15, wherein the constituents to be removed from the water are lipidic compounds (long chain fatty acids (LCFA)).

17. The method of claim 15, wherein the constituents to be removed are organic compounds such as volatile fatty acids, ethanol and aromatic compounds.

18. The method of claim 15, wherein said gaseous compounds produced are mainly methane gas ($CH_4$) and carbon dioxide ($CO_2$) to form biogas (9).

19. The method of claim 15, wherein said biogas (9) is liberated from sludge in the at least one downer (6) due to turbulence.

20. The method of claim 15, wherein biogas is mainly produced in the riser section (8) of the reaction vessel (1) thus inducing the said natural gas lift effect.

21. The method of claim 15, wherein the liquid level inside the reaction vessel (1) is maintained using a vertically extended tube equipped with a siphon breaker to the required liquid level and connected to the purified water outlet(s) of the reaction vessel (1).

22. The method of claim 15, wherein the microbial population inside the reactor (1) consists of anaerobic hydrolysing bacteria, acidifying bacteria, acetogenic bacteria and methanogenic bacteria.

23. The method of claim 15, wherein the microbial population also comprises bacteria specialised in hydrolysing lipids and anaerobically oxidising long chain fatty acids.

* * * * *